(12) United States Patent
Beiriger (10) Patent No.: US 10,286,135 B2
(45) Date of Patent: May 14, 2019

(54) MEASURING CONDUCTIVITY OF A MEDICAL FLUID

(71) Applicant: Fresenius Medical Care Holdings, Inc., Waltham, MA (US)

(72) Inventor: Michael James Beiriger, Pittsburgh, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1448 days.

(21) Appl. No.: 14/228,999

(22) Filed: Mar. 28, 2014

(65) Prior Publication Data
US 2015/0273126 A1    Oct. 1, 2015

(51) Int. Cl.
*A61M 1/16*    (2006.01)
*A61M 1/28*    (2006.01)
(Continued)

(52) U.S. Cl.
CPC ............ *A61M 1/1601* (2014.02); *A61M 1/14* (2013.01); *A61M 1/1605* (2014.02);
(Continued)

(58) Field of Classification Search
CPC ............. A61M 1/1601; A61M 1/1605; A61M 1/3609; A61M 1/14; A61M 1/1696;
(Continued)

(56) References Cited

U.S. PATENT DOCUMENTS 1,406,372 A    12/1921    Grapp
1,689,432 A    12/1927    Hartwig
(Continued)

FOREIGN PATENT DOCUMENTS

EP    0311848    4/1989
EP    1277485    1/2003
(Continued)

OTHER PUBLICATIONS

Pykett, Ian L., "NMR Imaging in Medicine", Scientific American, 1982, pp. 78-88.
(Continued)

*Primary Examiner* — Heidi R Kelley
*Assistant Examiner* — Akash K Varma
(74) *Attorney, Agent, or Firm* — Fish & Richardson P.C.

(57) ABSTRACT

In certain aspects, a dialysis device includes a flow channel that includes a disposable flow-through container. The flow channel and the container contain a fluid and are in fluid communication with each other. The dialysis device also includes a toroid configured to accept, through an aperture of the toroid, at least a portion of the container. The dialysis device also includes an electromagnetic coil wrapped around the toroid, such that the coil passes around an outer surface and an inner surface of the toroid, and covers less than the entire circumference of the toroid. The coil is configured to generate an electromagnetic signal. The coil is also configured to concentrate the electromagnetic signal on the fluid in the container such that the electromagnetic signal traverses the container in a direction that is substantially parallel to the direction of flow of the flow channel. The coil is also configured to read the electromagnetic signal after it has traversed the fluid in the container.

22 Claims, 7 Drawing Sheets

(51) Int. Cl.
  *A61M 1/14* (2006.01)
  *G01N 27/02* (2006.01)
  *G01R 27/22* (2006.01)
  *A61M 1/36* (2006.01)

(52) U.S. Cl.
  CPC ............ *A61M 1/1696* (2013.01); *A61M 1/28* (2013.01); *A61M 1/3609* (2014.02); *G01N 27/023* (2013.01); *G01R 27/22* (2013.01); *A61M 2205/3317* (2013.01); *A61M 2205/3327* (2013.01)

(58) Field of Classification Search
  CPC   A61M 1/28; A61M 1/16; A61M 1/36; A61M 2205/3317; A61M 2205/3327; A61M 1/1656; A61M 1/1668; B01D 61/24; B01D 61/28; B01D 61/30; B01D 61/32
  USPC .......................................... 210/647
  See application file for complete search history.

(56) References Cited

U.S. PATENT DOCUMENTS

| | | |
|---|---|---|
| 2,107,173 A | 2/1938 | William |
| 3,130,289 A | 4/1964 | Lawrence |
| 3,605,783 A | 9/1971 | Pecker |
| 3,694,625 A | 9/1972 | Cole |
| 3,808,401 A | 4/1974 | Wright |
| 3,867,688 A * | 2/1975 | Koski .................. G01N 27/42 324/30 |
| 4,093,912 A | 6/1978 | Double et al. |
| 4,136,708 A | 1/1979 | Cosentino |
| 4,262,177 A | 4/1981 | Paxton et al. |
| 4,508,622 A | 4/1985 | Polaschegg |
| 4,613,820 A | 9/1986 | Edelstein et al. |
| 4,676,467 A | 6/1987 | Palsulich |
| 4,778,451 A | 10/1988 | Kamen |
| 4,808,161 A | 2/1989 | Kamen |
| 4,826,482 A | 5/1989 | Kamen |
| 4,869,286 A | 9/1989 | Williams et al. |
| 4,902,282 A | 2/1990 | Bellotti et al. |
| 4,902,877 A | 2/1990 | Grasso et al. |
| 4,950,134 A | 8/1990 | Bailey et al. |
| 4,976,162 A | 12/1990 | Kamen |
| 5,002,471 A | 3/1991 | Perlov |
| 5,024,756 A | 6/1991 | Sternby |
| 5,088,515 A | 2/1992 | Kamen |
| 5,100,554 A | 3/1992 | Polaschegg |
| 5,116,021 A | 5/1992 | Faust et al. |
| 5,146,713 A | 9/1992 | Grafius |
| 5,178,182 A | 1/1993 | Kamen |
| 5,193,990 A | 3/1993 | Kamen et al. |
| 5,211,201 A | 5/1993 | Kamen et al. |
| 5,241,985 A | 9/1993 | Faust et al. |
| 5,243,289 A | 9/1993 | Blum et al. |
| D351,470 S | 1/1994 | Scherer et al. |
| 5,311,899 A | 5/1994 | Isayama et al. |
| 5,324,422 A | 6/1994 | Colleran et al. |
| 5,344,392 A | 9/1994 | Senninger et al. |
| 5,350,357 A | 9/1994 | Kamen et al. |
| 5,353,837 A | 10/1994 | Faust |
| 5,395,351 A | 3/1995 | Munsch |
| 5,421,208 A | 6/1995 | Packard et al. |
| 5,421,823 A | 6/1995 | Kamen et al. |
| 5,431,626 A | 7/1995 | Bryant et al. |
| 5,438,510 A | 8/1995 | Bryant et al. |
| 5,447,286 A | 9/1995 | Kamen et al. |
| 5,474,683 A | 12/1995 | Bryant et al. |
| 5,486,286 A | 1/1996 | Peterson et al. |
| 5,540,265 A | 7/1996 | Polaschegg et al. |
| 5,567,320 A | 10/1996 | Goux et al. |
| 5,570,716 A | 11/1996 | Kamen et al. |
| 5,572,992 A | 11/1996 | Kankkunen et al. |
| 5,583,948 A | 12/1996 | Shibayama |
| 5,592,086 A | 1/1997 | Weinstock et al. |
| 5,628,908 A | 5/1997 | Kamen |
| 5,634,896 A | 6/1997 | Bryant et al. |
| 5,640,995 A | 6/1997 | Packard et al. |
| 5,641,405 A | 6/1997 | Keshaviah et al. |
| 5,641,892 A | 6/1997 | Larkins et al. |
| 5,713,865 A | 2/1998 | Manning et al. |
| 5,741,125 A | 4/1998 | Neftel et al. |
| 5,755,683 A | 5/1998 | Houle et al. |
| 5,771,914 A | 6/1998 | Ling et al. |
| 5,772,637 A | 6/1998 | Heinzmann et al. |
| 5,788,099 A | 8/1998 | Treu et al. |
| 5,925,011 A | 7/1999 | Faict et al. |
| 5,925,014 A | 7/1999 | Teeple, Jr. |
| 5,938,634 A | 8/1999 | Packard |
| 5,986,455 A | 11/1999 | Magnuson |
| 5,989,423 A | 11/1999 | Kamen |
| 5,997,502 A | 12/1999 | Reilly et al. |
| 6,036,680 A | 3/2000 | Home et al. |
| 6,041,801 A | 3/2000 | Gray et al. |
| 6,042,784 A | 3/2000 | Wamsiedler et al. |
| 6,065,941 A | 5/2000 | Gray et al. |
| 6,074,359 A | 6/2000 | Keshaviah et al. |
| 6,081,120 A | 6/2000 | Shen |
| 6,118,207 A | 9/2000 | Ormerod et al. |
| 6,126,831 A | 10/2000 | Goldau et al. |
| 6,164,621 A | 12/2000 | Bouchard et al. |
| 6,165,154 A | 12/2000 | Gray et al. |
| 6,187,199 B1 | 2/2001 | Goldau |
| 6,220,295 B1 | 4/2001 | Bouchard et al. |
| 6,223,130 B1 | 4/2001 | Gray et al. |
| 6,228,047 B1 | 5/2001 | Dadson |
| 6,316,864 B1 | 11/2001 | Ormerod |
| 6,343,614 B1 | 2/2002 | Gray et al. |
| 6,364,857 B1 | 4/2002 | Gray et al. |
| 6,382,923 B1 | 5/2002 | Gray |
| 6,404,197 B1 | 6/2002 | Anderson et al. |
| 6,406,276 B1 | 6/2002 | Normand et al. |
| 6,414,493 B1 | 7/2002 | Rezvani |
| 6,416,293 B1 | 7/2002 | Bouchard et al. |
| 6,459,175 B1 | 10/2002 | Potega et al. |
| 6,468,424 B1 | 10/2002 | Doenig et al. |
| 6,497,676 B1 | 12/2002 | Childers et al. |
| 6,503,062 B1 | 1/2003 | Gray et al. |
| 6,520,747 B2 | 2/2003 | Gray et al. |
| 6,558,343 B1 | 5/2003 | Neftel |
| 6,592,542 B2 | 7/2003 | Childers et al. |
| 6,595,944 B2 | 7/2003 | Balschat et al. |
| 6,604,908 B1 | 8/2003 | Bryant et al. |
| 6,614,008 B2 | 9/2003 | Tidrick |
| 6,648,845 B1 | 11/2003 | Gotch et al. |
| 6,653,841 B1 * | 11/2003 | Koerdt .................. G01N 27/023 324/445 |
| 6,663,359 B2 | 12/2003 | Gray |
| 6,685,831 B2 | 2/2004 | Doenig et al. |
| 6,702,774 B1 | 3/2004 | Polaschegg |
| 6,709,417 B1 | 3/2004 | Houle et al. |
| 6,726,656 B2 | 4/2004 | Kamen et al. |
| 6,746,514 B2 | 6/2004 | Bedingfield et al. |
| 6,749,403 B2 | 6/2004 | Bryant et al. |
| 6,764,761 B2 | 7/2004 | Eu et al. |
| 6,799,883 B1 | 10/2004 | Urquhart et al. |
| 6,808,369 B2 | 10/2004 | Gray et al. |
| 6,814,547 B2 | 11/2004 | Childers et al. |
| 6,860,866 B1 | 3/2005 | Graf et al. |
| 6,869,538 B2 | 3/2005 | Yu et al. |
| 6,911,007 B2 | 6/2005 | Nier et al. |
| 6,995,563 B2 | 2/2006 | Talutis |
| 7,078,909 B2 * | 7/2006 | Feng .................. G01N 27/023 324/127 |
| 7,279,903 B2 | 10/2007 | Quackenbush et al. |
| D556,909 S | 12/2007 | Reihanifam |
| D556,910 S | 12/2007 | Reihanifam |
| D576,281 S | 9/2008 | Reihanifam |
| 7,463,129 B1 | 12/2008 | Danby et al. |
| 7,661,293 B2 | 2/2010 | Dam |
| 7,661,294 B2 | 2/2010 | Dam |
| 7,788,047 B2 | 8/2010 | Schick et al. |
| 8,182,692 B2 | 5/2012 | Gotch |
| 8,324,900 B2 | 12/2012 | Helvoort et al. |

(56) References Cited

U.S. PATENT DOCUMENTS

| | | | |
|---|---|---|---|
| 8,353,870 B2 | 1/2013 | Levin et al. | |
| 8,409,864 B2 | 4/2013 | Ash | |
| 8,525,533 B2 | 9/2013 | Sullivan | |
| 2002/0000793 A1 | 1/2002 | Hanaki | |
| 2002/0045851 A1 | 4/2002 | Suzuki et al. | |
| 2002/0107474 A1 | 8/2002 | Noack | |
| 2002/0147423 A1 | 10/2002 | Burbank et al. | |
| 2003/0018395 A1 | 1/2003 | Crnkovich et al. | |
| 2003/0028094 A1 | 2/2003 | Kumar et al. | |
| 2003/0029451 A1 | 2/2003 | Blair et al. | |
| 2003/0040700 A1 | 2/2003 | Hickle et al. | |
| 2003/0042181 A1 | 3/2003 | Metzner | |
| 2003/0085621 A1 | 5/2003 | Potega | |
| 2003/0111457 A1 | 6/2003 | Tidrick | |
| 2003/0130606 A1 | 7/2003 | Tuck | |
| 2003/0136189 A1 | 7/2003 | Lauman et al. | |
| 2003/0195453 A1* | 10/2003 | Han | A61M 1/3653 604/5.01 |
| 2003/0200812 A1 | 10/2003 | Kuhn et al. | |
| 2003/0204162 A1 | 10/2003 | Childers et al. | |
| 2003/0217957 A1 | 11/2003 | Bowman et al. | |
| 2003/0217961 A1 | 11/2003 | Hopping | |
| 2003/0217975 A1 | 11/2003 | Yu et al. | |
| 2003/0218623 A1 | 11/2003 | Krensky et al. | |
| 2003/0220599 A1 | 11/2003 | Lundtveit | |
| 2003/0220605 A1 | 11/2003 | Bowman et al. | |
| 2003/0220607 A1 | 11/2003 | Busby et al. | |
| 2003/0220608 A1 | 11/2003 | Huitt et al. | |
| 2003/0220609 A1 | 11/2003 | Childers et al. | |
| 2003/0220627 A1 | 11/2003 | Distler et al. | |
| 2004/0010223 A1 | 1/2004 | Busby et al. | |
| 2004/0012391 A1 | 1/2004 | Vaughan et al. | |
| 2004/0019313 A1 | 1/2004 | Childers et al. | |
| 2004/0019320 A1 | 1/2004 | Childers et al. | |
| 2004/0024301 A1 | 2/2004 | Hockett et al. | |
| 2004/0031756 A1 | 2/2004 | Suzuki et al. | |
| 2004/0064080 A1 | 4/2004 | Cruz et al. | |
| 2004/0067161 A1 | 4/2004 | Axelsson | |
| 2004/0082903 A1 | 4/2004 | Micheli | |
| 2004/0085173 A1 | 5/2004 | Decristofaro et al. | |
| 2004/0122353 A1 | 6/2004 | Shahmirian et al. | |
| 2004/0135078 A1 | 7/2004 | Mandro et al. | |
| 2004/0193031 A1 | 9/2004 | Fuller | |
| 2004/0195190 A1 | 10/2004 | Min et al. | |
| 2005/0025797 A1 | 2/2005 | Wang et al. | |
| 2005/0127919 A1 | 6/2005 | Feng et al. | |
| 2005/0151422 A1 | 7/2005 | Gilmour | |
| 2005/0230292 A1 | 10/2005 | Beden et al. | |
| 2005/0234381 A1 | 10/2005 | Niemetz et al. | |
| 2005/0242034 A1 | 11/2005 | Connell et al. | |
| 2006/0195064 A1 | 8/2006 | Plahey et al. | |
| 2007/0020701 A1 | 1/2007 | Menon et al. | |
| 2007/0244382 A1 | 10/2007 | Robinson et al. | |
| 2007/0278155 A1 | 12/2007 | Lo et al. | |
| 2008/0015493 A1 | 1/2008 | Childers et al. | |
| 2008/0077074 A1 | 3/2008 | Keenan et al. | |
| 2008/0136415 A1 | 6/2008 | Rooij et al. | |
| 2009/0128155 A1 | 5/2009 | Otake et al. | |
| 2009/0167304 A1 | 7/2009 | Prado et al. | |
| 2009/0267617 A1* | 10/2009 | Seyfi | G01N 27/023 324/655 |
| 2009/0278537 A1 | 11/2009 | Harvey | |
| 2010/0072994 A1 | 3/2010 | Lee et al. | |
| 2010/0164498 A1 | 7/2010 | Helvoort et al. | |
| 2011/0004143 A1 | 1/2011 | Beiriger et al. | |
| 2011/0009800 A1 | 1/2011 | Dam | |
| 2011/0043209 A1 | 2/2011 | Zhu | |
| 2011/0097987 A1 | 4/2011 | Weissleder et al. | |
| 2011/0199097 A1 | 8/2011 | Hartsough | |
| 2011/0304416 A1 | 12/2011 | Warner et al. | |
| 2012/0068723 A1 | 3/2012 | Sullivan | |
| 2012/0100546 A1 | 4/2012 | Lowery et al. | |
| 2012/0164644 A1 | 6/2012 | Neely et al. | |
| 2012/0203476 A1 | 8/2012 | Dam | |
| 2012/0232471 A1 | 9/2012 | Chen et al. | |
| 2012/0258545 A1 | 10/2012 | Ash | |

FOREIGN PATENT DOCUMENTS

| | | |
|---|---|---|
| EP | 0887655 B1 | 3/2004 |
| WO | 9211046 | 7/1992 |
| WO | 9625214 | 8/1996 |
| WO | WO9961900 A1 | 12/1999 |
| WO | WO2001047415 A1 | 7/2001 |
| WO | WO2008001326 A1 | 1/2008 |
| WO | WO2010114932 A1 | 10/2010 |
| WO | WO2012022304 A1 | 2/2012 |
| WO | 2012108984 | 8/2012 |

OTHER PUBLICATIONS

Kim et al., "Multichannel transceiver dual-tuned RF coil for proton/sodium MR imaging of knee cartilage at 3 T", Magnetic Resonance Imaging, 30, 2012, pp. 562-571.

Price et al., "Development of tissue-targeted metabonomics—Part 1—Analytical considerations", Journal of Pharmaceutical and Biomedical Analysis, 46, 2008, pp. 737-747.

Notification of Transmittal of The International Search Report and The Written Opinion of the International Search Authority for corresponding PCT Application No. PCT/US2015/021550, dated Jun. 30, 2015, 13 pages.

Pang et al., "Common-Mode Differential-Mode (CMDM) Method for Double-Nuclear MR Signal Excitation and Reception at Ultra-high Fields", IEEE Trans Med Imaging, Jun. 20, 2011, pp. 1965-1973.

Notification of Transmittal of the International Search report and the Written Opinion of the International Searching Authority from corresponding PCT Application No. PCT/US2015/021550, dated Jun. 30, 2015, 13 pages.

Notification of Transmittal of the International Preliminary Report of Patentablity from the corresponding PCT Application No. PCT/US2015/021550, dated Oct. 4, 2016, 10 pages.

Labotka et al., "A Dialysis Cell for Nuclear Magnetic Resonance Spectroscopic Measurement of Protein-Small Molecule Binding", Anal. Biochem, vol. 191, pp. 376-383, 1990.

Buess et al., "Acoustic ringing effects in pulsed nuclear magnetic resonance probes", Rev. Sci. Instrum., vol. 48, No. 8, 1978, pp. 1151-1155.

Depaula et al., "Clinical consequences of an individualized dialysate sodium prescription in hemodialysis patients," Kidney International, vol. 66 (2004), pp. 1232-1238.

Gambro®, "Prismaflex™ anticipating care needs and taking our innovative response . . . to new heights", © 2004, Gambro, Inc., Lakewood, CO, 8 pages.

Gambro®, "DEHP-free cartridge blood sets," © Nov. 2004, Gambro, Inc., Lakewood, CO, 4 pages.

Gotch et al., "Mechanisms determining the ratio of conductivity clearance to urea clearance", Kidney International, vol. 66, Supplement 89 (2004), pp. S1-S24.

Sleep Safe™ Operating Instructions, Fresenius Medical Care, Aug. 2000.

Zhou et al., "Impact of sodium and ultrafiltration profiling on haemodialysis-related hypotension", NDT Advance Access published online on Sep. 5, 2006.

2008T Hemodialysis Machine Operator's Manual. P.N. 490122 Rev E, Fresenius Medical Care, 2008.

* cited by examiner

MEASURING CONDUCTIVITY OF A MEDICAL FLUID

TECHNICAL FIELD

This invention relates to measuring conductivity of a medical fluid.

BACKGROUND

During hemodialysis, impurities and toxins are removed from the blood of a patient by drawing the blood out of the patient through a blood access site, typically via a catheter, and then passing the blood through an artificial kidney (often referred to as a "dialyzer"). The artificial kidney includes a semi-permeable membrane that separates a first conduit from a second conduit. Generally, a dialysis solution (often referred to as a "dialysate") flows through the first conduit of the dialyzer while the patient's blood flows through the second conduit of the dialyzer, causing impurities and toxins to be transferred from the blood to the dialysate through the semi-permeable membrane. The impurities and toxins can, for example, be removed from the blood by a diffusion process. After passing through the dialyzer, the purified blood is then returned to the patient.

Maintaining a substantially constant concentration of sodium in the patient's blood throughout the hemodialysis treatment can help to reduce or prevent discomfort experienced by the patient. Therefore, sodium concentrations in the patient's blood and in the dialysate can be monitored during hemodialysis treatment.

SUMMARY

In one aspect, a dialysis device includes a flow channel that includes a disposable flow-through container. The flow channel and the container contain a fluid and are in fluid communication with each other. The dialysis device also includes a toroid configured to accept, through an aperture of the toroid, at least a portion of the container. The dialysis device also includes an electromagnetic coil wrapped around the toroid, such that the coil passes around an outer surface and an inner surface of the toroid, and covers less than the entire circumference of the toroid. The coil is configured to generate an electromagnetic signal. The coil is also configured to concentrate the electromagnetic signal on the fluid in the container such that the electromagnetic signal traverses the container in a direction that is substantially parallel to the direction of flow of the flow channel. The coil is also configured to read the electromagnetic signal after it has traversed the fluid in the container.

Implementations can include one or more of the following features.

In some implementations, the dialysis device also includes a second electromagnetic coil wrapped around the toroid, such that the second coil passes around an outer surface and an inner surface of the toroid, covers less than the entire circumference of the toroid, and resides in a position substantially opposite of the first electromagnetic coil. The second electromagnetic coil is configured to read the electromagnetic signal after it has traversed the fluid in the container.

In some implementations, the dialysis device also includes an oscillator for generating an input oscillating signal. The dialysis device also includes a first amplifier for modifying the input oscillating signal. The dialysis device also includes an excitation source for providing power to the coil. The dialysis device also includes a second amplifier for modifying the reading of the electromagnetic signal after it has traversed the fluid in the container to determine an output oscillating signal. The dialysis device also includes a computation device. The computation device is configured to receive the input oscillating signal from the oscillator. The computation device is also configured to receive the output oscillating signal from the second amplifier. The computation device is also configured to measure at least one electrical characteristic of the fluid in the container based on the input oscillating signal and the output oscillating signal. The coil generates the electromagnetic signal based on the modified input oscillating signal. The coil also reads the electromagnetic signal after it has traversed the fluid in the container. The coil also provides the reading of the electromagnetic signal to the second amplifier.

In some implementations, the disposable flow-through container is a cuvette with fixed dimensions.

In some implementations, the computation device is configured to receive a predetermined measurement of the container. The computation device is also configured to measure at least one electrical characteristic of the fluid in the container based on the input oscillating signal, the output oscillating signal, and the predetermined measurement.

In some implementations, the fluid is dialysate.

In some implementations, the dialysate is spent dialysate.

In some implementations, the fluid resides substantially stagnantly within the container for a period of time.

In some implementations, the fluid is blood.

In some implementations, the toroid is a ferrite toroid.

In some implementations, the disposable flow-through container includes a fluid inlet port through which the fluid enters the container from an inlet line of the flow channel, and a fluid outlet port through which the fluid exits the container to an outlet line of the flow channel.

In some implementations, the disposable flow-through container is replaced with an unused disposable flow-through container after use.

In some implementations, the computation device is configured to receive a direct measurement of the volume of the fluid in the container.

In some implementations, the container can be removed from the flow channel without disassembling the rest of the flow channel.

In some implementations, the container can be removed from the flow channel without damaging the flow channel.

In some implementations, the container can be removed from the flow channel without disrupting the rest of the flow channel.

In another aspect, a method includes using a dialysis fluid pump of a dialysis machine to deliver fluid through a flow channel that includes a disposable flow-through container. The flow channel and the container contain a fluid and are in fluid communication with each other. The method also includes introducing at least a portion of the container into an aperture of a toroid. The method also includes generating, by an electromagnetic coil wrapped around the toroid, such that the coil passes around an outer surface and an inner surface of the toroid, and covers less than the entire circumference of the toroid, an electromagnetic signal. The method also includes concentrating the electromagnetic signal on the fluid in the container such that the electromagnetic signal traverses the container in a direction that is substantially parallel to the direction of flow of the flow channel. The method also includes measuring at least one electrical characteristic of the fluid in the container.

Implementations can include one or more of the following features.

In some implementations, the method also includes receiving a predetermined measurement of the container. Measuring at least one electrical characteristic of the fluid in the container includes performing a calculation using an input electrical signal, an output electrical signal, and the predetermined measurement.

In another aspect, a peritoneal dialysis (PD) machine includes a dialysis fluid pump that is operable to pump dialysis fluid through a flow channel to a disposable flow-through container. The PD machine also includes a magnet assembly that generates a magnetic field. The magnet assembly defines a cavity configured to receive at least a portion of the container. The PD machine also includes a measurement device for measuring electrical characteristics of the fluid in the container. The magnet assembly concentrates the flux of the magnetic field on the dialysis fluid in the container so that the flux traverses the container in a direction that is substantially parallel to the direction of flow of the flow channel.

In another aspect, a dialysis device includes a flow channel. The flow channel includes an inlet line, an outlet line, and a disposable flow-through container. The container is configured to receive a fluid from the inlet line. The container is also configured to allow the fluid to accumulate in the container. The container is also configured to allow the fluid to exit the container through the outlet line. The dialysis device also includes a toroid configured to accept, through an aperture of the toroid, at least a portion of the container. The dialysis device also includes an electromagnetic coil wrapped around the toroid. The electromagnetic coil is configured to generate an electromagnetic signal. The electromagnetic coil is also configured to concentrate the electromagnetic signal on the fluid in the container. The fluid resides substantially stagnantly in the container for a period of time during which the electromagnetic signal is concentrated on the fluid. The electromagnetic coil is also configured to read the electromagnetic signal after it has traversed the fluid in the container.

In another aspect, a dialysis device includes a flow channel. The flow channel includes an inlet line, an outlet line, and a disposable flow-through container. The container is configured to receive a fluid from the inlet line. The container is also configured to allow the fluid to accumulate in the container. The container is also configured to allow the fluid to exit the container through the outlet line. The dialysis device also includes a toroid having a top surface configured to accept, from the top surface, through an aperture of the toroid, at least a portion of the container, such that the inlet line, the outlet line, and the rest of the container reside above the top surface of the toroid. The dialysis device also includes an electromagnetic coil wrapped around the toroid. The electromagnetic coil is configured to generate an electromagnetic signal. The electromagnetic coil is also configured to concentrate the electromagnetic signal on the fluid in the container. The electromagnetic coil is also configured to read the electromagnetic signal after it has traversed the fluid in the container.

The details of one or more implementations are set forth in the accompanying drawings and the description below. Other features, objects, and advantages will be apparent from the description and drawings, and from the claims.

DETAILED DESCRIPTION

In dialysis systems, the conductivity of dialysate can be measured, for example, for patient safety reasons. For example, the dialysate should have a conductivity that indicates that a certain amount and ratio of sodium bicarbonate is present, because an imbalance could impact the health of the patient and cause discomfort. A contactless sensor can measure the conductivity of the dialysate without making direct contact (e.g., via electrodes) with the fluid.

In some implementations, one or more electromagnetic coils wrapped around a toroid (e.g., a ferrite toroid) can generate an electromagnetic signal, and focus the electromagnetic signal across dialysate in a container with fixed dimensions. The container can be a uniform-sized cuvette. A measurement device (e.g., a second coil, or the same single coil) can be used to measure the signal after it has traversed the dialysate (e.g., an output signal). Measurements can include the amplitude of the signal and the phase shift of the signal (e.g., before and after it traverses the dialysate), among others.

One or more of the measurements can be used to determine electrical characteristics of the dialysate without making direct contact with the dialysate. The toroid can be arranged such that the container that contains the dialysate can be easily introduced to, and easily removed from the magnetic field. For example, an aperture in the toroid can accept the container. This can allow another dialysate container (e.g., a dialysate container used for the next patient) to be measured without the need for sterilizing the dialysate machine or excessive assembly and disassembly. The contactless conductivity sensor can allow for disposal of the dialysate container without disposing of expensive measurement devices (e.g., electrodes).

Figure 1:
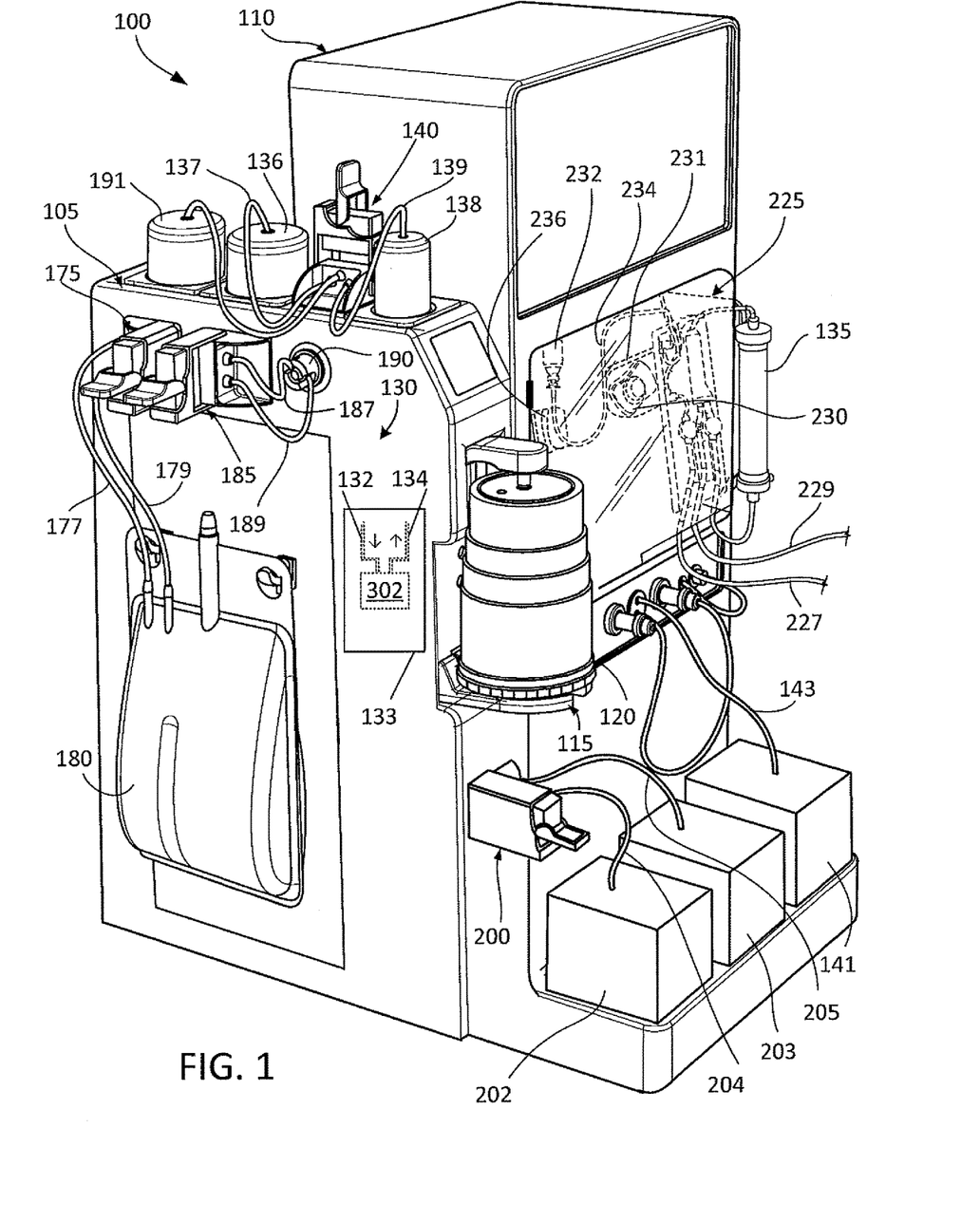
FIG. 1 is a perspective view of a hemodialysis system.

FIG. 1 shows a hemodialysis system 100 in which the conductivity of fluid (e.g., dialysate) can be measured, for example, using the techniques described above. The hemodialysis system 100 includes a module 105 fluidly coupled to a hemodialysis machine 110. The module 105 includes, among other things, a sorbent device holder 115 that holds a sorbent device 120. The module 105 also includes a collection unit 302 that includes an inlet line 132 and outlet line 134. As will be described in greater detail below, the module 105 is used to recycle spent dialysate so that the spent dialysate can be reused during a hemodialysis treatment. During use of the hemodialysis system 100, dialysate is pumped from the module 105 to the hemodialysis machine 110. The dialysate is then passed through a dialyzer 135 connected to the hemodialysis machine 110 at the same time that a dialysis patient's blood is passed through the dialyzer 135. As a result, toxins, such as urea, migrate across a permeable membrane (e.g., hollow fibers) of the dialyzer 135 from the patient's blood to the dialysate, producing spent dialysate (i.e., dialysate that contains toxins removed from the patient's blood). The spent dialysate is pumped to the module 105 where it passes through the sorbent device 120, which removes toxins from the spent dialysate. As a result of chemical reactions that occur within the sorbent device 120, the recycled dialysate exiting the sorbent device 120 typically contains gas, such as carbon dioxide. After exiting the sorbent device 120, the recycled dialysate travels into the module 105 and then is drawn into the collection unit 302 via the inlet line 132. The collection unit 302 resides within the module 105. The module 105 includes a door 133 that provides access to the collection unit 302 which resides inside the hemodialysis system 100. The recycled dialysate is then forced from the collection unit 302 back into the module 105 via the outlet line 134. The recycled dialysate is then cycled back through the dialysate circuit and reused to cleanse the dialysis patient's blood.

Certain desired substances (e.g., magnesium, calcium, potassium, and sodium) may be stripped from the dialysate as the dialysate passes through the sorbent device 120. Those stripped substances can be added to the dialysate exiting the sorbent device 120 (e.g., prior to drawing the dialysate into the collection unit 302). As shown in FIG. 1, an infusate solution container 136 and a sodium chloride solution container 138 are connected to a manifold 140 of the module 105 via fluid lines 137 and 139, respectively. The infusate solution (e.g., a solution including magnesium, calcium, and potassium) and sodium chloride can be drawn into the dialysate flowing within the module 105 by activating associated valves and pumps within the module 105. As shown in FIG. 1, a dilution water container 141 is connected to the dialysis machine 110 via a fluid line 143. In some cases, certain substances, such as sodium, may be added to, rather than stripped from, the dialysate as the dialysate passes through the sorbent device 120. As a result, the sodium concentration in the dialysate exiting the sorbent device 120 may exceed a maximum desired concentration. In such cases, dilution water can be added to dialysate that is exiting the hemodialysis machine 110 and flowing into the module 105 toward the sorbent device 120. The dilution water can be added to the dialysate exiting the hemodialysis machine 110 by activating a pump within the hemodialysis machine 110. Activating this pump draws the dilution water from the dilution water container 141 and fluid line 143 into the dialysate exiting the hemodialysis machine 110 such that the sodium concentration of the dialysate exiting the hemodialysis machine 110 (and eventually flowing through the module 105) is reduced, as will be described in greater detail below.

The sodium concentration of the dialysate passing through the dialyzer 135 affects (e.g., increases or decreases) the sodium concentration in the patient's blood. If the sodium concentration in the patient's blood falls outside a desired range, the patient may experience discomfort or illness. For this reason, a conductivity measurement device 300 (not shown in its entirety) may be positioned near or within the module 105 to measure the conductivity of dialysate after the dialysate exits the sorbent device 120. These conductivity readings can be used during treatment to determine the amount of sodium chloride solution or dilution water to be added to the recycled dialysate exiting the sorbent device 120. In particular, because the sodium in the dialysate is the predominant contributor to the conductivity of the dialysate, the sodium concentration of the dialysate can be determined or approximated based on the conductivity readings. The amount of sodium chloride solution or dilution water to add to the dialysate in order to achieve a desired sodium concentration within the dialysate can then be determined. The hemodialysis system 100 can contain more than one conductivity measurement device 300 for measuring various ions.

In addition to the manifolds 130 and 140, the module 105 includes a manifold 175 to which fluid lines 177, 179 extending from the bag 180 are connected and a manifold 185 to which fluid lines 187, 189 extending from an ammonium (NH4) sensor 190 are connected. The module 105 further includes a manifold 200 by which a fresh dialysate container 202 and a drain container 203 are connected to the module 105 via a fluid line 204 and a drain line 205, respectively. Each of manifolds 130, 140, 175, 185, and 200 can, for example, include projections on which fluid lines can be positioned to connect the various components described above to their respective manifold. Any of various other suitable connection mechanisms can alternatively or additionally be used to connect the fluid lines to the manifolds.

The manifold 175 allows dialysate to be transferred from the module 105 to the bag 180 and vice versa. In particular, using pumps and valves within the module 105, dialysate can be pumped into and suctioned out of the bag 180 via the fluid lines 177, 179 connected to the manifold 175. The manifold 185 permits dialysate to be transferred from the module 105 to the ammonium sensor 190 and vice versa. By activating pumps and valves within the module 105 in a desired manner, the dialysate can be pumped from the module 105 to the ammonium sensor 190 and can be drawn back to the module 105 from the ammonium sensor 190. By activating pumps and valves within the module, fluid can be drawn into the module 105 from the fresh dialysate container 202 via the fluid line 204, and fluid can be pumped from the module 105 to the drain container 203 via the drain line 205. With the sorbent device 120 positioned in the cartridge holder 115, as shown in FIG. 1, fluid circulating within the module 105 is allowed to pass through the sorbent device 120 to recycle the dialysate.

Still referring to FIG. 1, a blood component set 225 is secured to a front face of the hemodialysis machine 110. The blood component set 225 includes arterial and venous patient lines 227, 229 that are connected to a patient during treatment. The arterial patient line 227 is connected to an inlet port of the dialyzer 135 via a series of blood lines, and the venous patient line 229 is connected to an outlet port of the dialyzer 135 via a series of blood lines. A blood pump line 231 positioned between the arterial patient line 227 and the dialyzer 135 is operably connected to a peristaltic blood pump 230 extending from the front face of the hemodialysis machine 110. The peristaltic blood pump 230 can be operated to pump blood through the various blood lines and components of the blood component set 225. In particular, operation of the blood pump 230 draws blood from the patient through the arterial patient line 227. The blood continues through a series of blood lines and blood components (e.g., sensors) to the dialyzer 135. The blood exits the dialyzer 135 and passes through another series of blood lines and components (e.g., sensors) and then is returned to the patient via the venous patient line 229.

As the blood is pumped through the various blood lines and components of the blood component set 225, it may be desirable to inject certain substances, such as drugs and/or saline into the blood lines. As shown in FIG. 1, a drug vial (e.g., a heparin vial) 232 is connected to one of the blood lines via a drug delivery line 234. The drug delivery line 234 is threaded through a peristaltic drug pump 236, which can be used to deliver the drug from the vial 232 to the blood circuit during treatment. A saline bag may also be connected to a blood line of the blood component set 225 via a priming line. This arrangement allows saline to be delivered through the blood circuit formed by the blood lines and components of the blood component set when desired. In some examples, the blood component 225 may include a conductivity device positioned upstream from the dialyzer 135 to measure the conductivity of blood.

Figure 2:
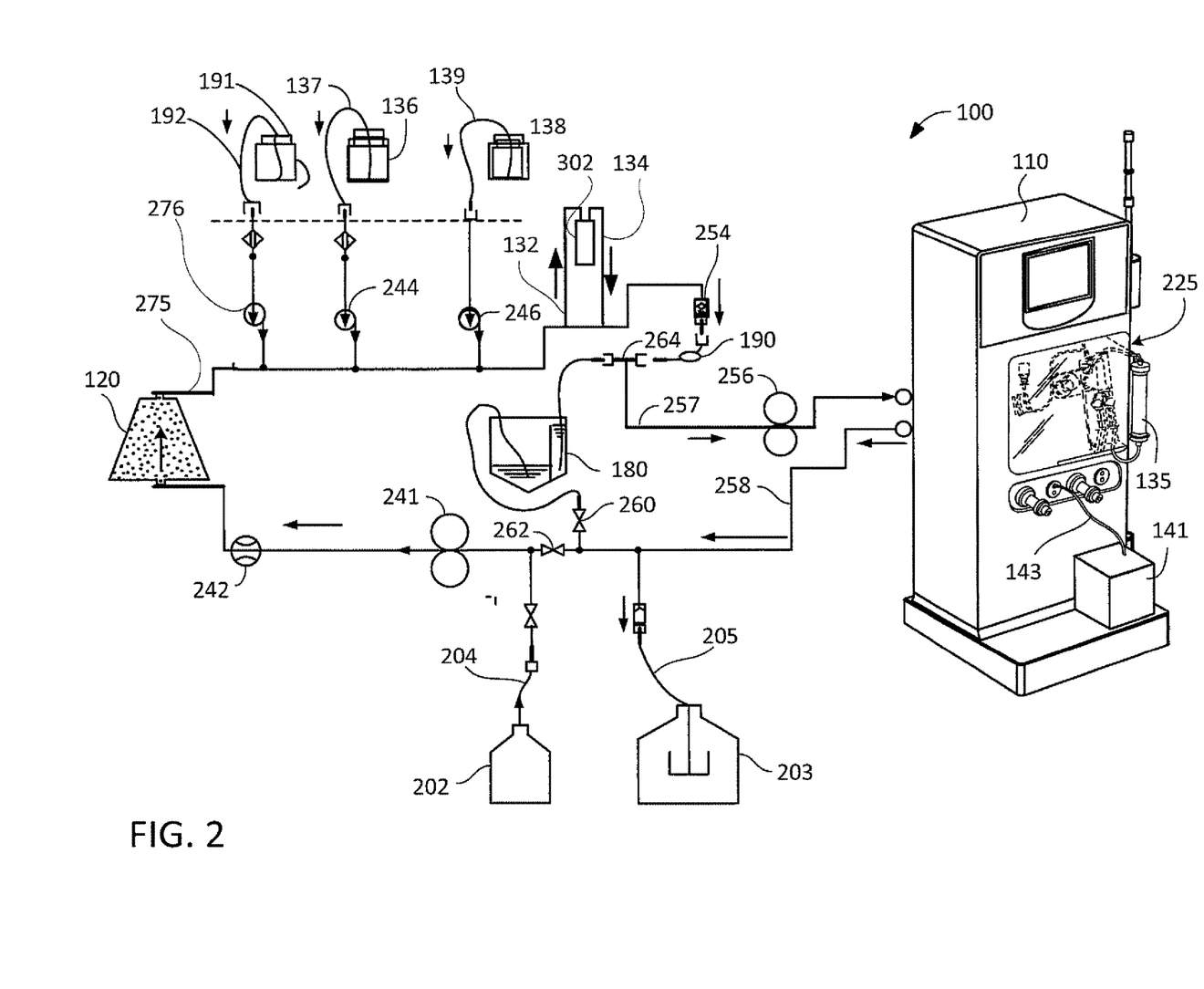
FIG. 2 is a diagram of fluid flow in the hemodialysis system of FIG. 1.

FIG. 2 schematically illustrates the various components of the module 105 connected to the hemodialysis machine 110. Referring to FIG. 2, a method of performing hemodialysis will now be described. Prior to beginning the dialysis treatment, fresh dialysate is drawn into the module 105 from the fresh dialysate container 202 by selectively activating a pump 241 and various valves of the module 105. The fresh dialysate is then circulated through the module 105 by the pump 241. Prior to reaching the sorbent device 120, the dialysate passes through a flow meter 242 that is configured to measure the flow rate of the dialysate passing therethrough. A signal representing the flow rate of the dialysate can be transmitted from the flow meter 242 to a control unit (e.g., a microprocessor). The control unit can use the detected flow rate of the dialysate to control metering of the infusate solution into the dialysate.

As the dialysate passes through the sorbent device 120, certain substances, such as calcium, magnesium, potassium, and sodium may be stripped from the dialysate. As discussed above, the sorbent device 120 is also adapted to remove toxins, such as urea, from fluid flowing therethrough, but while the fresh dialysate from the fresh dialysate container 202 would generally not contain any such toxins, it would have some capacity to purify dialysate, allowing, for example, tap water to be used as dialysate.

The infusate solution, which includes magnesium, calcium, and potassium, is then pumped into the fluid output line 275 from the infusate solution container 136 by activating a pump 244. As discussed above, the infusate solution can be added to the dialysate to restore concentrations of magnesium, calcium, and potassium to desired levels. Maintaining the concentration of these substances within the dialysis solution, such as calcium, magnesium, potassium, and sodium, can help to prevent the patient from experiencing discomfort during and after the treatment.

After introducing the infusate solution into the dialysate, the mixture of the dialysate and infusate solution continues to flow through the fluid output line 275 and passes into the collection unit 302 of the conductivity measurement device 300 (not shown in its entirety) via the inlet line 132. The conductivity of the dialysate is measured by the conductivity measurement device 300 (e.g., using the techniques described below), and is returned to the fluid output line 275 via the outlet line 134. The conductivity measurement can be used to determine the concentration of sodium bicarbonate within the dialysate. Maintaining proper concentrations of sodium bicarbonate can help reduce adverse health effects and prevent discomfort experienced by the patient. A pump 246 can then be activated in a manner to introduce sodium chloride solution into the fluid output line 275 from the sodium chloride solution container 138 if the conductivity reading indicates that the sodium level in the dialysate is lower than desired. The pump 246 can be operated in a manner to meter a desired volume of sodium chloride solution into the dialysate at a desired rate.

Similarly, a pump internal to the hemodialysis machine 110 can be activated to inject dilution water (e.g., tap water) from the dilution water container 141 into the dialysate exiting the hemodialysis machine 110 and entering the module 105 if the conductivity reading indicates that the sodium level in the dialysate is higher than desired. This dilution water pump can be operated in a manner to meter a desired volume of the dilution water into the dialysate at a desired flow rate.

A microprocessor (which may include the previously mentioned control unit or a different processing device) is connected to the flow meter 242, the conductivity measurement device 300, and the pumps 241, 244, 246, 256 and 276. The microprocessor is also connected to the dilution water pump inside the hemodialysis machine 110. The measured flow rate of the dialysate is transmitted in the form of a signal from the flow meter 242 to the microprocessor. The microprocessor adjusts operation of the pumps 241 and 256 based on the measured flow rate at the flow meter 242 to ensure that a prescribed dialysate flow rate is achieved. The microprocessor also controls the pump 244 as a function of the flow rate of the dialysate measured by the flow meter 242. This arrangement helps to ensure that a desired amount of the infusate is added to the dialysate, and thus helps to ensure a desired proportion of the infusate to the dialysate.

In response to receiving the signals from the conductivity measurement device 300, the microprocessor sends signals to the pumps 244 and 246 to cause some of the sodium chloride solution, if desired, to be introduced into the fluid output line 275. Similarly, in response to receiving these signals from the conductivity measurement device 300, the microprocessor can cause the dilution water pump in the hemodialysis machine 110 to pump dilution water, if desired, into the dialysate exiting the hemodialysis machine 110 and entering the module 105. As a result, the amount of sodium chloride and/or dilution water delivered to the dialysate can better achieve a desired sodium concentration within the dialysate (e.g., a sodium concentration that closely matches the sodium concentration prescribed by the dialysis patient's physician).

After passing through the conductivity measurement device 300, the dialysate passes through a check valve 254 and into the ammonium sensor 190, which detects ammonium levels within the dialysate.

After filling the bag 180 to a desired level with dialysate having a desired concentration of calcium, magnesium, potassium, and sodium, a pump 256 is activated to draw the dialysate from the bag 180 into the hemodialysis machine 110 via fluid line 257.

The dialysate is circulated through the hemodialysis machine 110 and passes through the dialyzer 135 connected to the hemodialysis machine 110. At the same time, a patient's blood is circulated through the blood component set 225, including the dialyzer 135, connected to the hemodialysis machine 110. As a result, toxins, such as urea, are transferred across a permeable membrane (e.g., permeable microtubes) of the dialyzer 135 from the patient's blood to the dialysate. The spent dialysate exiting the dialyzer 135 is then routed back to the module 105.

The spent dialysate passes through a fluid line 258 in the module 105. Depending on the desired volume of dialysate to be cycled back to the dialysis machine, some of the spent dialysate can be routed to a spent dialysate chamber of the bag 180 via open valve 260 while the remainder of spent dialysate is routed toward the sorbent device via open valve 262. As a result of the dialysis, for example, fluid from the patient may be added to the dialysate as the dialysate passes through the dialyzer 135. Thus, routing some of the spent dialysate to the bag 180 can help to ensure that a substantially constant volume of dialysate is circulated through the module 105 and/or the hemodialysis machine 110 throughout treatment. The pump 241 along the fluid line 258 forces the volume of the spent dialysate that is not routed to the bag 180 into the sorbent device 120 via the cartridge holder 115. As the spent dialysate passes through the sorbent device 120, urea is removed from the spent dialysate. Calcium, magnesium, and potassium are also stripped from the spent dialysate by the sorbent device 120.

In the manner discussed above, after the recycled dialysate exits the sorbent device 120, the infusate solution is introduced into the recycled dialysate and, based on the conductivity reading at the conductivity measurement device 300, sodium chloride may be added to the recycled dialysate. Sodium chloride may alternatively be added before the dialysate enters the sorbent device 120. Similarly, dilution water can be added to the spent dialysate exiting the hemodialysis machine 110 and entering the module 105 based on the reading at the conductivity measurement device 300. In the initial stages of treatment, sodium levels in the recycled dialysate tend to be lower than desired due to the tendency of the sorbent device 120 to strip sodium from the dialysate passing therethrough. Consequently, in the early stages of the treatment, sodium chloride will typically be injected into a fluid line to increase the concentration of sodium in the recycled dialysate. In later stages of the treatment, however, the sorbent device 120 may contain high levels of sodium and thus release sodium into the spent dialysate as the spent dialysate passes through the sorbent device 120. This can lead to higher than desired levels of sodium in the recycled dialysate passing through the fluid output line 275. In such cases, dilution water is injected into the spent dialysate exiting the hemodialysis machine 110 and entering the module 105 to lower the sodium concentration of the spent dialysate. This spent dialysate then travels through the module 105 to the sorbent device 120 where the dilution water and spent dialysate are filtered.

Injecting the dilution water into the spent dialysate before the spent dialysate passes through the sorbent device 120 to be filtered allows the use of tap water as the dilution water because the tap water will be filtered and purified as it passes through the sorbent device 120. This arrangement permits the hemodialysis system 100 to be operated with a readily available supply of dilution water and without the need for storing large volumes of dilution water on site.

After flowing past the conductivity measurement device 300, the recycled dialysate passes through the check valve 254 and into the ammonium sensor 190. After exiting the ammonium sensor 190, some of the recycled dialysate is routed to the bag 180 and some of the recycled dialysate is routed to the hemodialysis machine 110.

In order to ensure that an equal amount of fluid enters and exits the hemodialysis machine 110, a T-valve 264 is adapted to route a portion of the dialysate to the hemodialysis machine 110 via the fluid line 257 and to route excess dialysate to the fresh dialysate chamber of the bag 180. Because the flow rate of the dialysate at the T-valve 264 is generally greater than the rate at which the dialysate is being pulled into the hemodialysis machine 110, there will typically be excess dialysate passing through the T-valve 264 and that excess dialysate will be routed to the bag 180 where it is collected for later use.

The dialysate that is delivered to the hemodialysis machine 110 again passes through the dialyzer where toxins are transferred from the patient's blood to the dialysate. The spent dialysate is then routed back to the module and the process is repeated until a desired amount of toxins has been removed from the patient's blood.

After completing the patient's treatment, the dialysate can be removed from the bag 180. For example, the pumps and valves of the module 105 can be operated in a manner to pump the dialysate from the bag 180 into the drain container 203 or into a plumbing drain. Emptying the bag 180 can allow the user to more easily handle the bag 180 after treatment due to the decreased weight.

After draining the bag 180 to a desired level, the external components (e.g., the sorbent device 120, the infusate container 136, the collection unit 302, the sodium chloride container 138, the bag 180, the dialysate container 202, the drain container 203, and their associated fluid lines), which are constructed as disposable, single use components, are disconnected from the module 105 and discarded.

Figure 3:
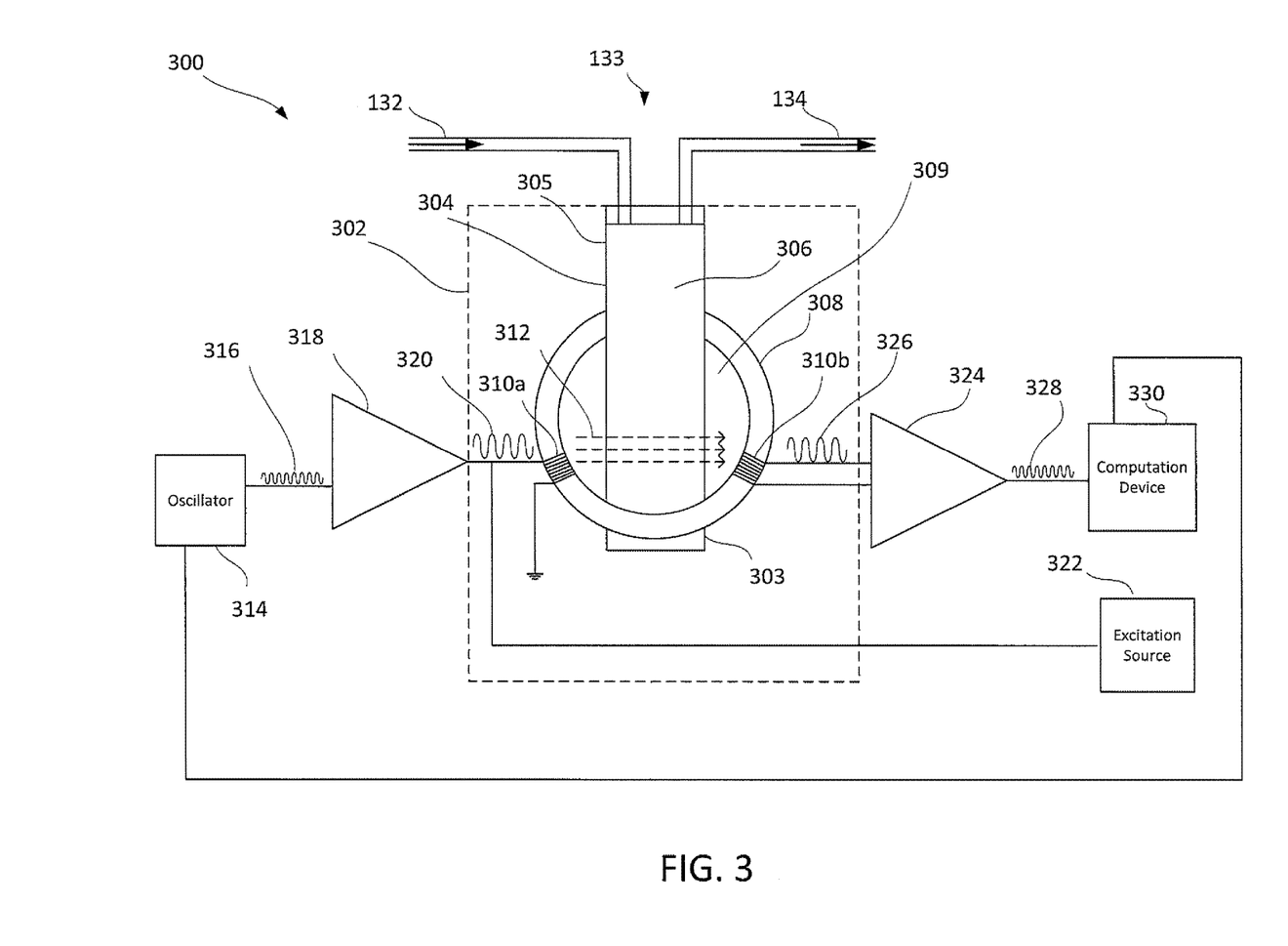
FIG. 3 is a diagram of an example of a device of the hemodialysis system of FIG. 1 for measuring conductivity of a fluid.

FIG. 3 shows a conductivity measurement device 300 with which the module 105 of the hemodialysis system 100 can be equipped for measuring the conductivity of the fluid (e.g., dialysate) in the collection unit 302. Fluid 306 (e.g., dialysate) flows into the collection unit 302 through a flow channel 133. The flow channel 133 includes an inlet line 132, an outlet line 134, and a flow-through container 304 (sometimes called a cuvette) that are all in fluid communication with each other. The flow-through container 304 includes a fluid inlet port and a fluid outlet port. The fluid 306 enters the flow-through container 304 from the inlet line 132 through the fluid inlet port, and the fluid 306 exits the flow-through container 304 to the outlet line 134 through the fluid outlet port. The fluid 306 flows through the flow-through container 304 so that its conductivity can be measured in the flow-through container 304.

The flow-through container 304 can be disposable. We use the term "disposable" to refer, for example, to a flow-through container 304 that is intended to be used on perhaps one occasion and no more than a few different occasions. The disposable flow-through container 304 may be used only once (e.g., for a single patient), thrown away after use, and replaced with a new disposable flow-through container 304. A disposable flow-through container 304 might not be cleaned after use; if a clean disposable flow-through container 304 is required, the dirty disposable flow-through container 304 is replaced with a clean disposable flow-through container 304. The disposable flow-through container 304 may be relatively cheap to manufacture, such that frequently replacing the disposable flow-through container 304 with a new disposable flow-through container 304 does not result in excessive costs.

The flow-through container 304 may be a container with fixed dimensions. The flow-through container 304 can be made of a rigid material. The flow-through container 304 can be made of a material suitable for containing a fluid. Examples of suitable materials for the flow-through container 304 include glass, plastic, and quartz, although there are a number of other suitable materials.

A toroid 308 is positioned near the flow-through container 304. The toroid 308 is configured to accept at least a portion of the flow-through container 304 (e.g., through an aperture 309 of the toroid 308). The toroid 308 can reside inside the collection unit 302 (a configuration shown in FIG. 3), or outside the collection unit 302 (a configuration not shown). The flow-through container 304 resides in the aperture 309 of the toroid 308, while substantially all of the rest of the flow channel 133 resides outside of the aperture 309 of the toroid 308, towards the surface of the toroid 308 from which the flow-through container 304 enters the aperture 309 of the toroid 308 (e.g., above the toroid). The inlet line 132 and the outlet line 134 both reside towards the same surface of the toroid 308.

The flow-through container 304 can be easily removable from the aperture 309 of the toroid 308 without damaging the rest of the flow channel 133, disassembling the rest of the flow channel 133, or otherwise disrupting the rest of the flow channel 133. The flow-through container 304 can be easily removable from the flow channel 133, and replaced with another flow-through container 304, without damaging the rest of the flow channel 133, disassembling the rest of the flow channel 133, or otherwise disrupting the rest of the flow channel 133. In this way, the conductivity of the fluid 306 can be measured without any portion of the flow channel 133, other than the flow-through container 304, residing in the aperture 309 of the toroid 308. This configuration can simplify the process of introducing the flow-through container 304 to, and removing the flow-through container 304 from, the aperture 309 of the toroid 308.

Figure 4:
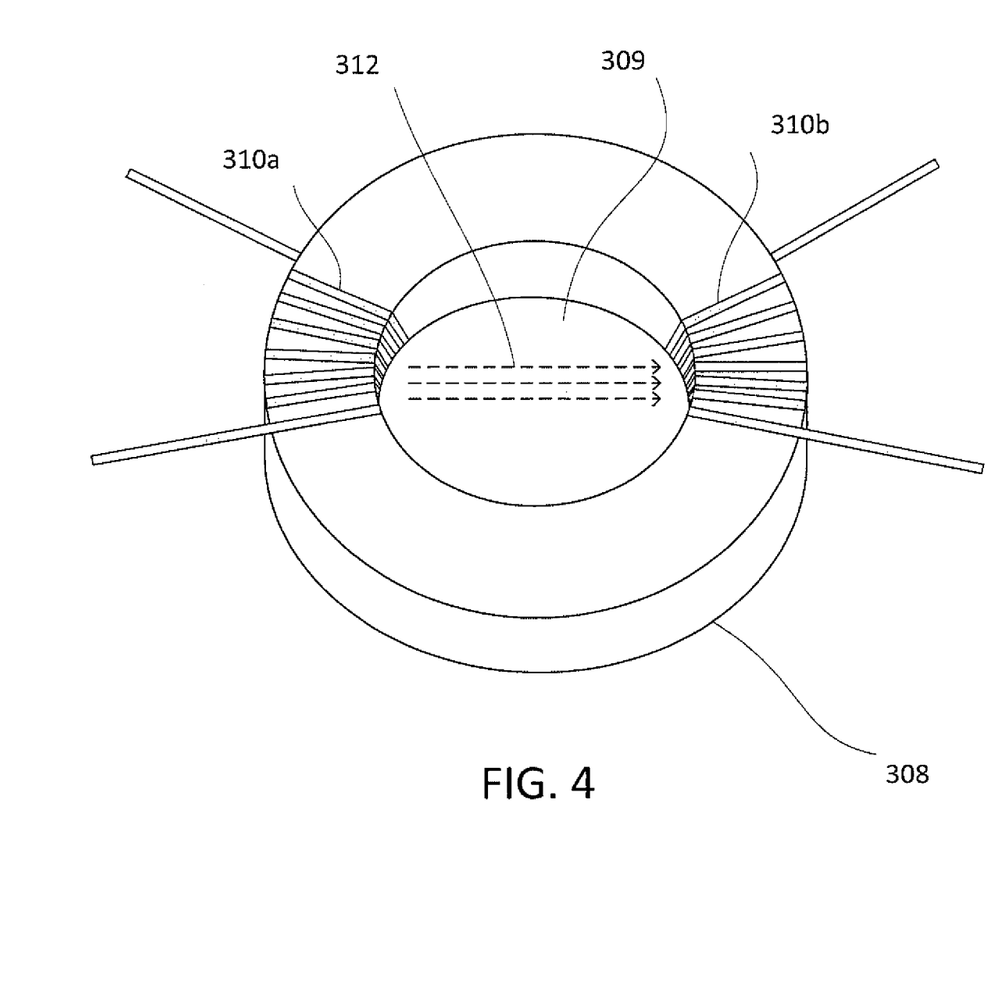
FIG. 4 is a diagram of an example of a toroid of the conductivity measuring device of FIG. 3.

The toroid 308 illustrated in FIG. 3 is a ring that has an aperture 309. The cross-section of the toroid 308 can be any shape suitable for a core of an electromagnetic coil (e.g., a first electromagnetic coil 310a and a second electromagnetic coil 310b). In some examples, the toroid 308 is a ring with a rectangular cross-section, as shown in FIG. 4. The rectangular cross-section may have rounded corners. The toroid 308 can alternatively be a ring with a circular cross-section. The toroid 308 can be made of any material suitable for a core of an electromagnetic coil. Examples of suitable materials for the toroid 308 include ferrite and iron, although there are a number of other suitable materials.

As shown in FIG. 4, a first electromagnetic coil 310a is wrapped around a portion of the toroid 308 a number of times, such that the first coil 310a passes around the outer surface and the inner surface of the toroid 308. The first coil 310a may cover less than the entire circumference of the toroid 308. The first coil 310a can be made of a conductive material (e.g., copper). Among other things, the materials used for the first coil 310a and the toroid 308, and the number of times the first coil 310a is wrapped around a portion of the toroid 308, define the electromagnetic characteristics of the first coil 310a.

A second electromagnetic coil 310b is similarly wrapped around a portion of the toroid 308 a number of times, such that the second coil 310b passes around the outer surface and the inner surface of the toroid 308. The second coil 310b may cover less than the entire circumference of the toroid 308. The second coil 310b can be made of the same material as the first coil 310a, or a different material. The second coil 310b can be wrapped around the toroid 308 the same number of times as the first coil 310a, or a different number of times. In some examples, the first coil 310a and the second coil 310b are wrapped around the toroid 308 on opposite ends of the toroid 308.

The properties of the toroid can be manipulated for improved focusing capabilities. Different portions of the toroid 308 can be made of different materials (e.g., the first coil 310a may be wrapped around a portion of the toroid 308 made of a first material and the second coil 310b may be wrapped around a portion of the toroid 308 made of a second material).

Referring back to FIG. 3, the first coil 310a is configured to generate an electromagnetic signal 312. An oscillator 314 can generate an input oscillating signal 316. A first amplifier 318 can accept the input oscillating signal 316, modify it, and provide a modified input oscillating signal 320 to the first coil 310a. An excitation source 322 can power the first coil 310a. Once powered, the first coil 310a can generate an electromagnetic signal 312 based on the modified input oscillating signal 320. The first coil 310a can concentrate the electromagnetic signal 312 on the fluid 306 in the flow-through container 304. In particular, the first coil 310a can concentrate the electromagnetic signal 312 such that the electromagnetic signal 312 traverses the flow-through container 304 in a direction that is substantially parallel to the direction of flow of the flow channel 133.

The first amplifier 318 can modify the amplitude, frequency, or phase of the input oscillating signal 316. The modified input oscillating signal 320 may be appropriate for measuring a conductivity of interest at a particular amplitude, frequency, or phase. One or more of the amplitude, frequency, or phase of the modified input oscillating signal 320 can provide improved measurement resolution of the conductivity of interest relative to the unmodified input oscillating signal 316. For example, if the conductivity measurement is expected to be a relatively large value, the amplitude of the input oscillating signal 316 may be increased by the first amplifier 318. On the other hand, if the conductivity measurement is expected to be a relatively small value, the amplitude of the input oscillating signal 316 may be decreased by the first amplifier 318. The first amplifier 318 can also cause the input oscillating signal 316 to be modified to sweep across a frequency range.

The flow-through container 304, the toroid 308, and the first coil 310a are positioned such that the electromagnetic signal 312 generated by the first coil 310a traverses the fluid 306 in the flow-through container 304. The electromagnetic signal 312 traverses the fluid 306 in an area of the flow-through container 304 where the fluid 306 resides substantially stagnantly for a period of time. In some examples, as explained above, fluid 306 can enter the flow-through container 304 from the inlet line 132 through the fluid inlet port, and fluid 306 can exit the flow-through container 304 to the outlet line 134 through the fluid outlet port. The fluid 306 may be more stagnant towards the bottom portion 303 of the flow-through container 304 than the top portion 305. The flow-through container 304, the toroid 308, and the first coil 310a may be positioned such that the electromagnetic signal 312 generated by the first coil 310a traverses the fluid in the flow-through container 304 at a portion of the flow-through container 304 where the fluid is the most stagnant. The fluid 306 does not actively flow through the aperture 309 of the toroid 308 (e.g., entering from one surface of the toroid 308, flowing through the aperture 309 of the toroid 308, leaving from the opposite surface of the toroid 308, and flowing away from the opposite surface of the toroid 308) but instead, remains substantially stagnant within the flow-through container 304, at least a portion of which resides in the aperture 309 of the toroid 308. When the fluid 306 is stagnant, it is less likely to contain bubbles. Bubbles can corrupt the conductivity measurement by displacing fluid 306 that would otherwise occupy the locations of the bubbles.

The toroid 308 and the first coil 310a can focus the electromagnetic signal 312 so that it traverses the fluid 306 in the flow-through container 304 at the desired location. The toroid 308 can have a low reluctance. That is, a magnetic field travels substantially inside the material of the toroid, and little magnetic field travels around the toroid outside of the material. At the gap of the toroid, the magnetic field is forced to cross the gap to maintain a closed loop field. The flow-through container 304 is positioned in the gap such that a known quantity of fluid 306 resides in the gap. A smaller gap of the toroid 308 results in a more narrowly focused electromagnetic signal 312 that traverses the fluid 306.

The first coil 310a that generates the electromagnetic signal 312 may be configured to read the electromagnetic signal 312 after it traverses the fluid 306 in the flow-through container 304. We sometimes refer to the form of the electromagnetic signal 312 after traversing the fluid 306 as the output electromagnetic signal 326. Alternatively, the second coil 310b can be configured to read the output electromagnetic signal 326 (as shown in FIGS. 3 and 4).

The electromagnetic signal 312 traversing the fluid 306 can cause the electromagnetic signal 312 to be altered. Characteristics of the fluid 306 (e.g., conductivity, impedance, volume, dimensions) contribute to the degree of alteration of the electromagnetic signal 312. Also, factors that are unrelated to the electromagnetic signal 312 traversing the fluid 306 can contribute to the degree of alteration of the electromagnetic signal 312 (e.g., the frequency of the electromagnetic signal 312, explained in more detail later). As a result, the output electromagnetic signal 326 can be different from the electromagnetic signal 312.

Figure 5:
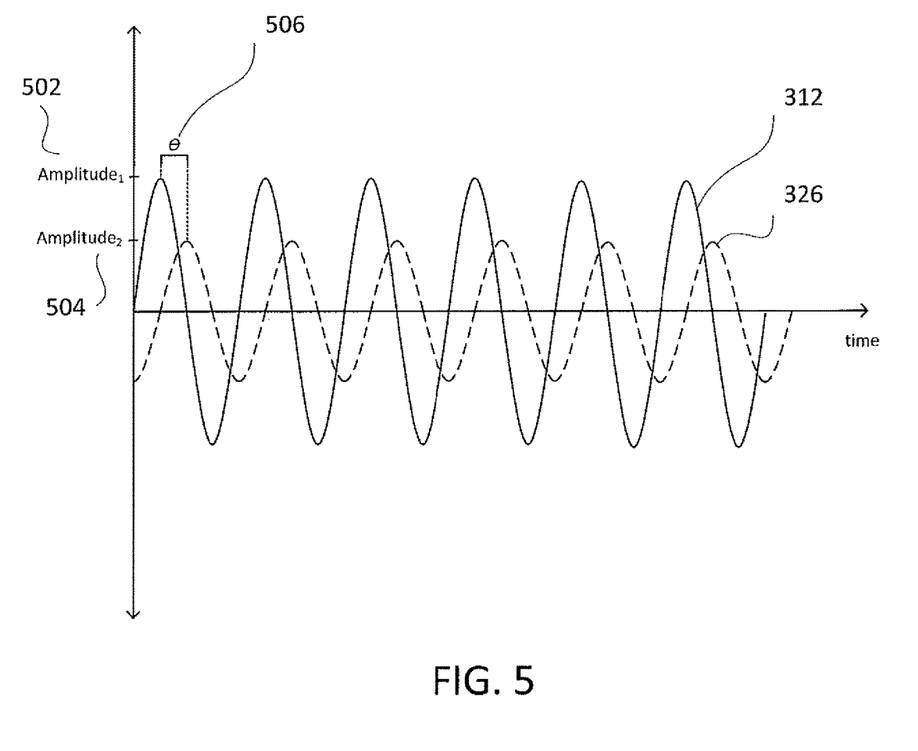
FIG. 5 is an example representation of electromagnetic signals generated by the conductivity measuring device of FIG. 3.

FIG. 5 shows a representation of an electromagnetic signal 312 and an output electromagnetic signal 326. The amplitude of the output electromagnetic signal 326 (e.g., Amplitude$_1$ 502) is different from the amplitude of the electromagnetic signal 312 (e.g., Amplitude$_2$ 504). There is also a phase shift (represented by θ 506) between the output electromagnetic signal 326 and the electromagnetic signal 312.

Whether, and to what degree, the electromagnetic signal 312 changes after traversing the fluid 306 can depend on the frequency of the electromagnetic signal 312. For example, a relatively high frequency electromagnetic signal 312 (e.g., in the order of MHz) can have lesser ability to penetrate the fluid 306, which can result in an output electromagnetic signal 326 that is significantly different from the electromagnetic signal 312, and a relatively low frequency electromagnetic signal 312 (e.g., in the order of KHz) can have greater ability to penetrate the fluid 306, which can result in an output electromagnetic signal 326 that is not very different from the electromagnetic signal 312. The relationship between the degree of change of electromagnetic signals 312 of different frequencies, and the frequency differences of the electromagnetic signals 312, may not be linear.

Figure 6A:
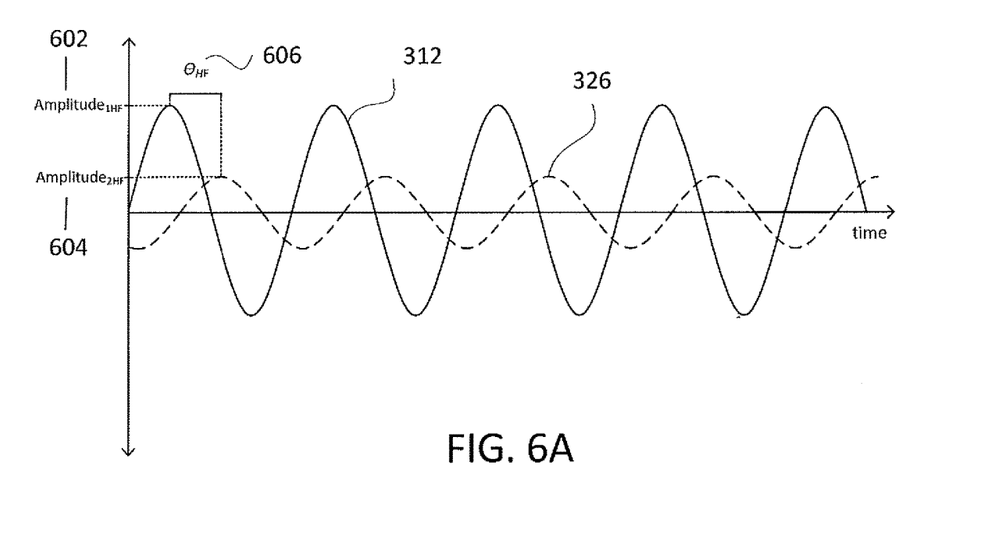
FIGS. 6a-b are example representations of electromagnetic signals generated by the conductivity measuring device of FIG. 3.
Figure 6B:
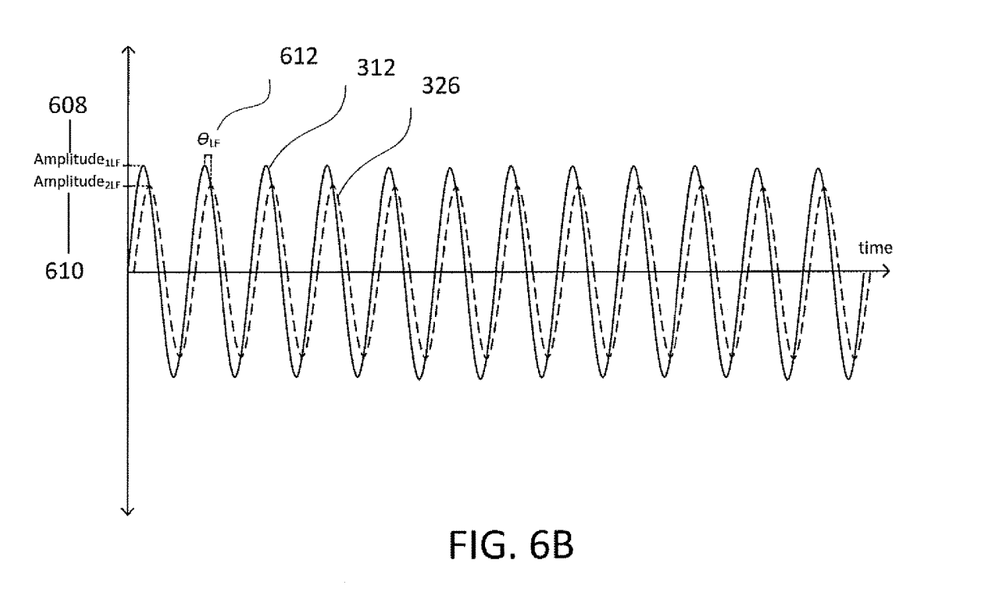

FIGS. 6a and 6b show representations of electromagnetic signals 312 and output electromagnetic signals 326. The electromagnetic signal 312 in FIG. 6a is substantially similar to the electromagnetic signal 312 in FIG. 6b except for its frequency. The characteristics of the fluid 306 that is being traversed, and any other testing conditions, are also substantially similar. Thus, in the representations shown in FIGS. 6a and 6b, we are observing only the effect that the frequency of the electromagnetic signal 312 has on the output magnetic signal 326.

In FIG. 6a, the electromagnetic signal 312 has a relatively high frequency, thus having lesser ability to penetrate the fluid 306. In FIG. 6b, the electromagnetic signal 312 has a relatively low frequency, thus having greater ability to penetrate the fluid 306. As a result, the difference between Amplitude$_{1HF}$ 602 and Amplitude$_{2HF}$ 604 is greater than the difference between Amplitude$_{1LF}$ 608 and Amplitude$_{2LF}$ 610. Also, the phase shift represented by θ$_{HF}$ 606 is greater than the phase shift represented by θ$_{LF}$ 612. A computation device 330 (explained in more detail below) can take the frequency of the electromagnetic signal 312 into account when determining the conductivity of the fluid 306. For example, the computation device 330 can arrive at the same value for the conductivity of the fluid 306 by using the information represented in FIG. 6a as it can by using the information represented in FIG. 6b.

A particular toroid 308 and first coil 310a (and sometimes also the second coil 310b) can be used when the frequency of the electromagnetic signal 312 is within a particular range. A toroid 308 made of a certain material, or having certain dimensions, may be suitable for a particular frequency range. A first coil 310a (and sometimes also the second coil 310b) made of a certain material, having certain dimensions, or wrapped around the toroid 308 a certain number of times, may be suitable for a particular frequency range.

In the example shown in FIG. 3, the second coil 310b reads the output electromagnetic signal 326. A second amplifier 324 can accept the output electromagnetic signal 326, modify it, and provide an output oscillating signal 328 to the computation device 330. The second amplifier 324 can modify the amplitude, frequency, or phase of the output electromagnetic signal 326. A modified output electromagnetic signal (e.g., the output oscillating signal 328) may be more suitable for the computation device 330 to receive. In some examples, the second amplifier 324 modifies only the amplitude of the output electromagnetic signal 326. The second amplifier 324 can also be combined with a filter to remove unwanted signals.

The computation device 330 can be configured to receive the input oscillating signal 316 from the oscillator 314 and the output oscillating signal 328 from the second amplifier 324. The computation device 330 can also be configured to receive a measurement of the flow-through container 304. The measurement of the flow-through container 304 can be used to determine the volume of the flow-through container 304. The computation device 330 can use the measurement of the flow-through container 304 to determine the volume of the fluid 306 in the flow-through container 304. The computation device 330 can use the measurement of the flow-through container 304, the received input oscillating signal 316, and the received output oscillating signal 328 to measure one or more electrical characteristics of the fluid (explained in more detail below). Alternatively, the computation device 330 can be configured to receive a direct measurement of the volume of fluid 306 in the flow-through container 304. In some examples, the measurement of the flow-through container 304, or the measurement of the volume of fluid 306 in the flow through container 304, is predetermined (e.g., the measurement is not active).

As mentioned above, characteristics of the fluid 306 (e.g., conductivity, volume, dimensions) can contribute to the degree in which the electromagnetic signal 312 is altered (e.g., transformed into the output electromagnetic signal 326). Factors that are unrelated to the electromagnetic signal 312 traversing the fluid 306 can also contribute to the degree in which the electromagnetic signal 312 is altered, such as the frequency of the electromagnetic signal 312. The computation device 330 can be configured to determine the conductivity of the fluid 306 in the flow-through container 304. Conductivity of the fluid 306 is a measure of the fluid's 306 ability to conduct electricity, and can be used, for example, to measure the ionic content in the fluid 306.

The computation device 330 is configured to determine at least one electrical characteristic of the fluid 306 to calculate the conductivity of the fluid 306. The computation device 330 can measure the impedance and the permittivity of the fluid 306. Permittivity of the fluid 306 causes an impedance change of the fluid 306. The impedance change may vary depending on the frequency of the electromagnetic signal 312. In some examples, the computation device 330 takes into account one or more of the following when measuring the at least one electrical characteristic of the fluid 306: characteristics of the first amplifier 318, the input oscillating signal 316, the modified input oscillating signal 320, the electromagnetic signal 312, the frequency of the electromagnetic signal 312, characteristics of the first coil 310a and the second coil 310b, characteristics of the toroid 308, the measurement of the volume of fluid 306 in the flow-through container 304, the measurement of the flow-through container 304, a measurement of the stagnancy of the fluid 306, the output electromagnetic signal 326, the output oscillating signal 328, the degree of difference between the amplitudes of the of the output electromagnetic signal 326 and the electromagnetic signal, the phase shift between the output electromagnetic signal 326 and the electromagnetic signal 312, and characteristics of the second amplifier 324, although there are a number of other factors that the computation device 330 can take into account when measuring the at least one electrical characteristic of the fluid 306. The computation device 330 can perform a calculation that involves the at least one electrical characteristic of the fluid 306 to determine the conductivity of the fluid 306.

In some examples, the computation device 330 can be configured to determine the conductivity of the fluid 306 in the flow-through container 304 based on information related to the input oscillating signal 316 and information related to the output oscillating signal 328 without considering the modified input oscillating signal 320, the output electromagnetic signal 326, or the characteristics of the first amplifier 318 or the second amplifier 324. As mentioned above, factors that are unrelated to the electromagnetic signal 312 traversing the fluid 306 can contribute to the degree in which the electromagnetic signal 312 is altered. These factors can be mitigated by making a baseline conductivity measurement of a fluid 306 having a known conductivity to come up with an adjustment factor, and applying the adjustment factor to subsequent conductivity measurements.

Figure 7:
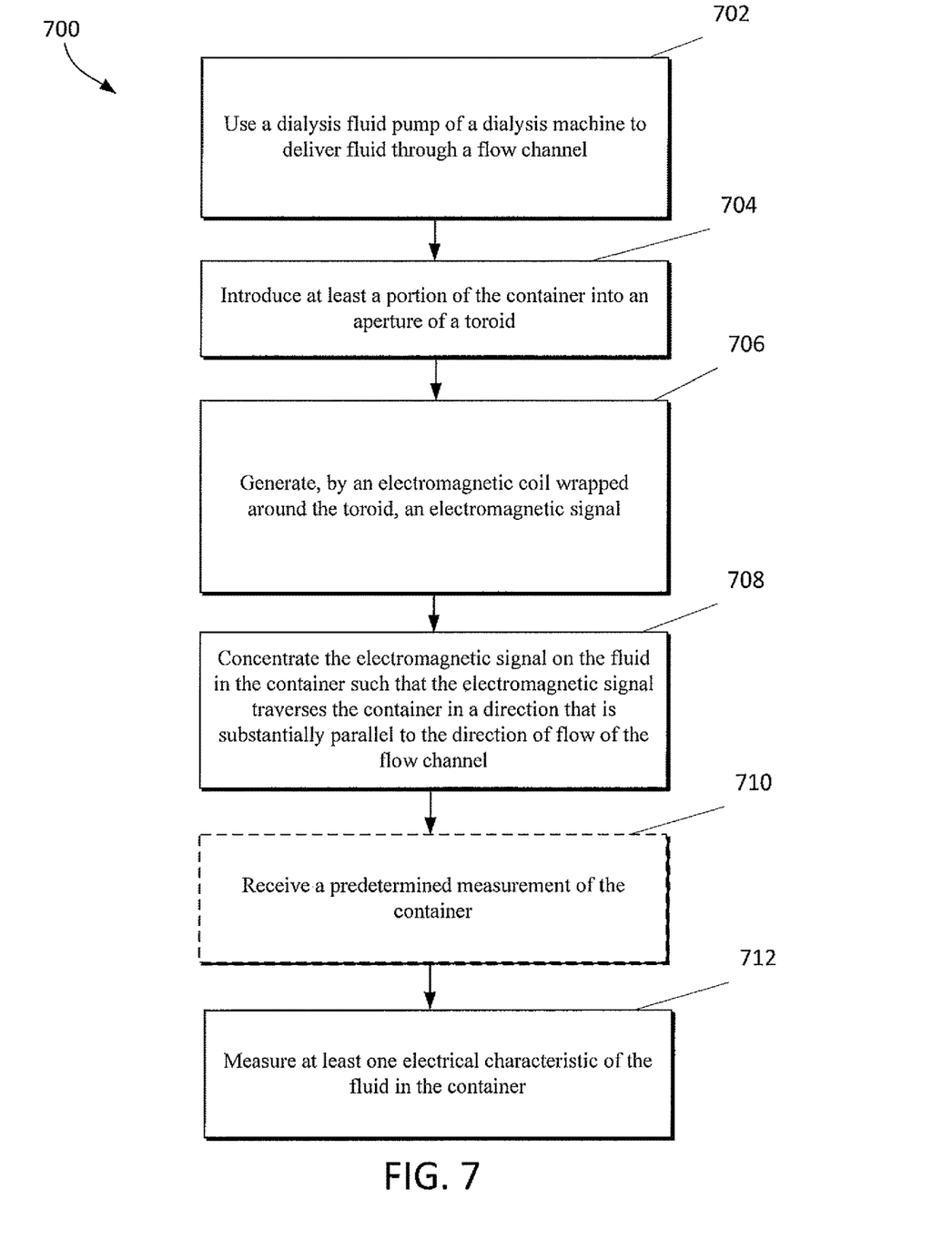
FIG. 7 is a flow chart illustrating a technique for measuring at least one electrical characteristic of a dialysis fluid using the conductivity measuring device of FIG. 3.

FIG. 7 is a flowchart illustrating a technique for measuring at least one electrical characteristic of a fluid. This technique can be used with a dialysis system, for example, the hemodialysis system 100 shown in FIG. 1. A dialysis fluid pump of a dialysis machine is used to deliver fluid through a flow channel (502). The flow channel includes an inlet line, and outlet line, and a disposable flow-through container, sometimes called a cuvette. The flow channel and the flow-through container contain a fluid and are in fluid communication with each other. The fluid enters the flow-through container from the inlet line and exits the flow-through container from the outlet line. The fluid resides in the flow-through container for a period of time. The flow-through container may have fixed dimensions. The fluid may be dialysate or another type of fluid used in a medical context.

At least a portion of the container is introduced into an aperture of a toroid (504). The toroid can be a ferrite toroid. The fluid resides substantial stagnantly in the container for a period of time. The fluid does not actively flow through the aperture of the toroid. That is, the fluid does not enter the aperture from one surface of the toroid, flow through the aperture of the toroid, leave from the opposite surface of the toroid, and flow away from the opposite surface of the toroid.

An electromagnetic signal is generated by an electromagnetic coil wrapped around the toroid (506). An oscillator generates an input electrical signal (e.g., the input oscillating signal) that is provided to the coil. An amplifier can modify the input electrical signal before it is provided to the coil. An excitation source powers the coil, and the coil generates an electromagnetic signal that is based on the input electrical signal. The coil can pass around an outer surface and an inner surface of the toroid, and can cover less than the entire circumference of the toroid.

The electromagnetic signal is concentrated on the fluid in the container (508). The electromagnetic signal traverses the container in a direction that is substantially parallel to the direction of flow of the flow channel. The toroid can help focus the electromagnetic signal on the fluid in the container. The fluid may be substantially stagnant within the container while the electromagnetic signal is concentrated on the fluid.

The electromagnetic signal traversing the fluid can cause the electromagnetic signal to be altered. The electrical characteristics of the fluid can contribute to the degree of alteration of the electromagnetic signal. Also, factors unrelated to the electromagnetic signal traversing the fluid can contribute to the degree of alteration of the electromagnetic signal. We sometimes refer to the form of the electromagnetic signal after traversing the fluid as the output electromagnetic signal.

In some examples, a second electromagnetic coil reads the output electromagnetic signal. Alternatively, the same electromagnetic coil that generates the electromagnetic signal reads the output electromagnetic signal. A second amplifier can accept the output electromagnetic signal and modify it to create an output electrical signal (e.g., the output oscillating signal).

Optionally, a predetermined measurement of the container is received (510). The predetermined measurement of the container can be a volume of the container. The predetermined measurement of the container can be used to determine the volume of the fluid 306 in the container. The volume of the fluid, along with other readings, can be used to calculate at least one electrical characteristic of the fluid. For example, when the electrical characteristic of the fluid in the container is measured, a calculation can be performed using an input electrical signal (e.g., the input oscillating signal 316), an output electrical signal (e.g., the output oscillating signal 328), and the predetermined measurement of the container.

At least one electrical characteristic of the fluid in the container is measured (block 512). A computation device measures the at least one electrical characteristic of the fluid using the input electrical signal and the output electrical signal. The differences between the input electrical signal and the output electrical signal can reflect the degree of alteration of the electromagnetic signal as a result of traversing the fluid. Because the electrical characteristics of the fluid contribute to the degree of alteration of the electromagnetic signal as a result of traversing the fluid, the input electrical signal and the output electrical signal can be used to measure the at least one electrical characteristic of the fluid.

The computation device can also use the predetermined measurement of the container to measure the at least one electrical characteristic of the fluid. The at least one electrical characteristic of the fluid can be the impedance or the permittivity of the fluid. The at least one electrical characteristic can be used to calculate the conductivity of the fluid.

While the conductivity measuring device has been described as part of a hemodialysis system, conductivity measurement devices of the type described herein can alternatively be used in other types of medical systems, such as peritoneal dialysis systems, heart lung machines, chemotherapy systems, or any other system that introduces fluid into the body.

While the conductivity measuring device has been described as measuring the conductivity of spent dialysate, conductivity measurement devices of the type described herein can be used to measure the conductivity of other types of medical fluids, such as blood, plasma, saline, or urine, to name a few.

A number of embodiments of the invention have been described. Nevertheless, it will be understood that various modifications may be made without departing from the spirit and scope of the invention. Accordingly, other embodiments are within the scope of the following claims.

What is claimed is:

1. A dialysis device comprising:
a flow channel that comprises a disposable flow-through container, the flow channel and the container containing a fluid and in fluid communication with each other, wherein the disposable flow-through container comprises a fluid inlet port through which the fluid enters the container from an inlet line of the flow channel, and a fluid outlet port through which the fluid exits the container to an outlet line of the flow channel;
a toroid configured to accept, through an aperture of the toroid, at least a portion of the container;
an electromagnetic coil wrapped around the toroid, such that the coil passes around an outer surface and an inner surface of the toroid, and covers less than the entire circumference of the toroid, the coil configured to:
generate an electromagnetic signal;
concentrate the electromagnetic signal on the fluid in the container such that the electromagnetic signal traverses the container in a direction that is substantially parallel to the direction of flow of the flow channel, wherein a portion of the fluid resides substantially stagnantly within the container while flow is maintained in the inlet line and the outlet line; and
read the electromagnetic signal after it has traversed the fluid in the container.

2. The dialysis device of claim 1, further comprising a second electromagnetic coil wrapped around the toroid, such that the second coil passes around an outer surface and an inner surface of the toroid, covers less than the entire circumference of the toroid, and resides in a position substantially opposite of the first electromagnetic coil, wherein the second electromagnetic coil is configured to read the electromagnetic signal after it has traversed the fluid in the container.

3. The dialysis device of claim 1, further comprising:
an oscillator for generating an input oscillating signal;
a first amplifier for modifying the input oscillating signal;
an excitation source for providing power to the coil;
a second amplifier for modifying the reading of the electromagnetic signal after it has traversed the fluid in the container to determine an output oscillating signal; and
a computation device configured to:
receive the input oscillating signal from the oscillator;
receive the output oscillating signal from the second amplifier; and
measure at least one electrical characteristic of the fluid in the container based on the input oscillating signal and the output oscillating signal,
wherein the coil:
generates the electromagnetic signal based on the modified input oscillating signal;
reads the electromagnetic signal after it has traversed the fluid in the container; and
provides the reading of the electromagnetic signal to the second amplifier.

4. The dialysis device of claim 3, wherein the disposable flow-through container is a cuvette with fixed dimensions.

5. The dialysis device of claim 4, wherein the computation device is configured to:
receive a predetermined measurement of the container, and
measure at least one electrical characteristic of the fluid in the container based on the input oscillating signal, the output oscillating signal, and the predetermined measurement.

6. The dialysis device of claim 1, wherein the fluid is dialysate.

7. The dialysis device of claim 6, wherein the dialysate is spent dialysate.

8. The dialysis device of claim 1, wherein the fluid resides substantially stagnantly within the container for a period of time.

9. The dialysis device of claim 1, wherein the fluid is blood.

10. The dialysis device of claim 1, wherein the toroid is a ferrite toroid.

11. The dialysis device of claim 1, wherein the disposable flow-through container is replaced with an unused disposable flow-through container after use.

12. The dialysis device of claim 1, wherein the computation device is configured to receive a direct measurement of the volume of the fluid in the container.

13. The dialysis device of claim 1, wherein the container can be removed from the flow channel without disassembling the rest of the flow channel.

14. The dialysis device of claim 1, wherein the container can be removed from the flow channel without damaging the flow channel.

15. The dialysis device of claim 1, wherein the container can be removed from the flow channel without disrupting the rest of the flow channel.

16. A method comprising:
using a dialysis fluid pump of a dialysis machine to deliver fluid through a flow channel that comprises a disposable flow-through container, the flow channel and the container containing a fluid and in fluid communication with each other, wherein the disposable flow-through container comprises a fluid inlet port through which the fluid enters the container from an inlet line of the flow channel, and a fluid outlet port through which the fluid exits the container to an outlet line of the flow channel;
introducing at least a portion of the container into an aperture of a toroid;
generating, by an electromagnetic coil wrapped around the toroid, such that the coil passes around an outer surface and an inner surface of the toroid, and covers less than the entire circumference of the toroid, an electromagnetic signal;
concentrating the electromagnetic signal on the fluid in the container such that the electromagnetic signal traverses the container in a direction that is substantially parallel to the direction of flow of the flow channel, wherein a portion of the fluid resides substantially stagnantly within the container while flow is maintained in the inlet line and the outlet line; and
measuring at least one electrical characteristic of the fluid in the container.

17. The method of claim 16, comprising
receiving a predetermined measurement of the container, wherein measuring at least one electrical characteristic of the fluid in the container comprises performing a calculation using an input electrical signal, an output electrical signal, and the predetermined measurement.

18. The dialysis device of claim 1, wherein the dialysis device is a peritoneal dialysis (PD) machine.

19. A dialysis device comprising:
a flow channel that comprises an inlet line, an outlet line, and a disposable flow-through container, wherein the disposable flow-through container comprises a fluid inlet port through which the fluid enters the container from the inlet line, and a fluid outlet port through which the fluid exits the container to the outlet line, the container configured to
allow the fluid to accumulate in the container; and
a toroid configured to accept, through an aperture of the toroid, at least a portion of the container; and
an electromagnetic coil wrapped around the toroid configured to:
generate an electromagnetic signal;
concentrate the electromagnetic signal on the fluid in the container, wherein a portion of the fluid resides substantially stagnantly within the container while flow is maintained in the inlet line and the outlet line; and
read the electromagnetic signal after it has traversed the fluid in the container.

20. A dialysis device comprising:
a flow channel that comprises an inlet line, an outlet line, and a disposable flow-through container, wherein the disposable flow-through container comprises a fluid inlet port through which the fluid enters the container from the inlet line, and a fluid outlet port through which the fluid exits the container to the outlet line, the container configured to
allow the fluid to accumulate in the container; and
a toroid having a top surface configured to accept, from the top surface, through an aperture of the toroid, at least a portion of the container, such that the inlet line, the outlet line, and the rest of the container reside above the top surface of the toroid; and
an electromagnetic coil wrapped around the toroid configured to:
generate an electromagnetic signal;
concentrate the electromagnetic signal on the fluid in the container, wherein a portion of the fluid resides substantially stagnantly within the container while flow is maintained in the inlet line and the outlet line; and
read the electromagnetic signal after it has traversed the fluid in the container.

21. The dialysis device of claim 1, wherein the flow-through container is removable from the flow channel.

22. The dialysis device of claim 1, wherein the flow-through container is configured to allow the fluid to accumulate in the container.

* * * * *

UNITED STATES PATENT AND TRADEMARK OFFICE
CERTIFICATE OF CORRECTION

PATENT NO. : 10,286,135 B2
APPLICATION NO. : 14/228999
DATED : May 14, 2019
INVENTOR(S) : Michael James Beiriger Page 1 of 1

It is certified that error appears in the above-identified patent and that said Letters Patent is hereby corrected as shown below:

In the Claims

In Claim 19, Column 19, Line 18, after "container;" delete "and".

In Claim 20, Column 20, Line 9, after "container;" delete "and".

Signed and Sealed this
Twenty-fourth Day of January, 2023

Katherine Kelly Vidal
*Director of the United States Patent and Trademark Office*